United States Patent
Koulikov

(10) Patent No.: US 10,921,242 B2
(45) Date of Patent: Feb. 16, 2021

(54) METHOD AND APPARATUS FOR INDETIFICATION OF COUNTERFEIT DRUGS, PHARMACEUTICALS, OR MEDICINES

(71) Applicant: Serguei Koulikov, Los Altos, CA (US)

(72) Inventor: Serguei Koulikov, Los Altos, CA (US)

( * ) Notice: Subject to any disclaimer, the term of this patent is extended or adjusted under 35 U.S.C. 154(b) by 351 days.

(21) Appl. No.: 15/856,149

(22) Filed: Dec. 28, 2017

(65) Prior Publication Data

US 2019/0025219 A1 Jan. 24, 2019

Related U.S. Application Data

(60) Provisional application No. 62/535,505, filed on Jul. 21, 2017.

(51) Int. Cl.

| | |
|---|---|
| *G01N 21/3504* | (2014.01) |
| *G01N 21/71* | (2006.01) |
| *G01N 33/15* | (2006.01) |
| *G01N 21/27* | (2006.01) |
| *G01N 21/31* | (2006.01) |
| *G01J 3/42* | (2006.01) |
| *G01N 21/39* | (2006.01) |
| *G01N 21/17* | (2006.01) |

(52) U.S. Cl.
CPC ............ *G01N 21/3504* (2013.01); *G01J 3/42* (2013.01); *G01N 21/27* (2013.01); *G01N 21/31* (2013.01); *G01N 21/39* (2013.01); *G01N 21/716* (2013.01); *G01N 33/15* (2013.01); *G01N 2021/1704* (2013.01); *G01N 2021/1748* (2013.01); *G01N 2021/399* (2013.01); *G01N 2201/0612* (2013.01)

(58) Field of Classification Search
None
See application file for complete search history.

(56) References Cited

U.S. PATENT DOCUMENTS

| | | | |
|---|---|---|---|
| 6,030,657 A | 2/2000 | Butland et al. | |
| 6,458,595 B1 | 10/2002 | Selinfreund | |
| 8,420,400 B2 | 4/2013 | Hayward et al. | |
| 8,543,411 B2 | 9/2013 | Koster | |
| 8,719,043 B2 | 5/2014 | Polli et al. | |
| 8,931,696 B2 | 1/2015 | Hood | |
| 9,233,049 B2 | 1/2016 | Siegel | |
| 9,476,839 B2 | 10/2016 | Ranieri et al. | |
| 9,651,533 B2 | 5/2017 | Islam | |
| 2005/0250216 A1* | 11/2005 | Liang | G01N 33/15 436/139 |

(Continued)

OTHER PUBLICATIONS

Rodionova et al., NIR-based approach to counterfeit-drug detection, Trends in Analytical Chemistry, 2010, vol. 29, No. 8, 795-803, Elsevier Ltd.

(Continued)

*Primary Examiner* — Shawn Decenzo

(57) ABSTRACT

Systems and methods for measuring the isotope ratio of one or more gaseous oxides produced during combustion of drugs, pharmaceuticals, or medicines aiming to detect counterfeit drugs, pharmaceuticals, or medicines based on comparison of the isotopic composition of the tested drugs, pharmaceuticals, or medicines with the isotopic composition of the authentic products.

11 Claims, 1 Drawing Sheet

(56) References Cited

U.S. PATENT DOCUMENTS

2018/0024074 A1    1/2018  Ranieri et al.

OTHER PUBLICATIONS

Yu et al., Characterization of drug authenticity using thin-layer chromatography imaging with a mobile phone, Journal of Pharmaceutical and Biomedical Analysis, 125 (2016) 85-93, Elsevier B.V.
Hall, Technology for combating counterfeit medicine, Pathogens and Global Health, 2012, vol. 106, No. 2, 73-76, W. S. Maney & Son Ltd.
Deisingh, Pharmaceutical counterfeiting, Analyst, 2005, 130, 271-279, The Royal Society of Chemistry.
Gupta et al., Laser-based measurements of 18O/16O stable isotope ratios ($\delta$18O) in wine samples, International Journal of Wine Research, 2013:5 47-54, Dove Press.
McCord et al., Universal HPLC Analysis for Counterfeit Medication: A Partnership of Purdue University and the Kilimanjaro School of Pharmacy, Purdue Journal of Service-Learning and International Engagement, vol. 2 : Iss. 1 , Article 7, 23-27.
Olsen et al., Screening for Counterfeit Drugs Using Near-Infrared Spectroscopy, Pharmaceutical Technology North America 26(6):62-71, Pharmtech.com.
Jasper et al., Stable Isotopic Analysis of Porcine, Bovine, and Ovine Heparins, Journal of Pharmaceutical Sciences 104:457-463, 2015, Wiley Periodicals, Inc.

\* cited by examiner

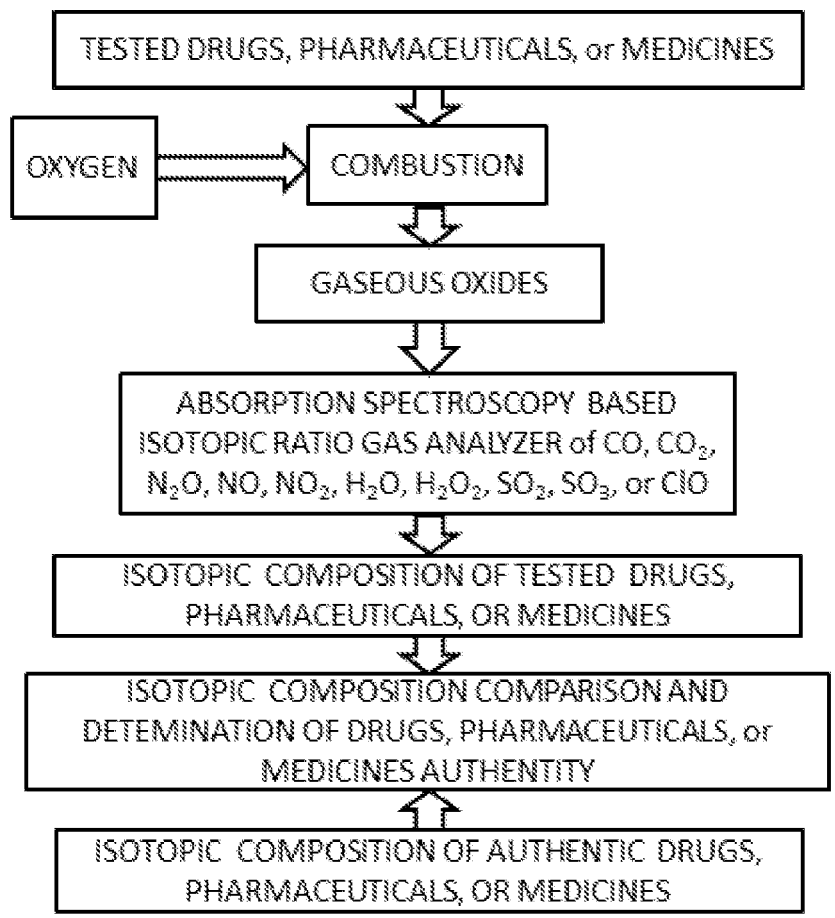

METHOD AND APPARATUS FOR INDETIFICATION OF COUNTERFEIT DRUGS, PHARMACEUTICALS, OR MEDICINES

CROSS-REFERENCES TO RELATED APPLICATIONS

This application claims the benefit of, and priority to, U.S. provisional Patent application No. 62/535,505 filed Jul. 21, 2017, the contents of which are hereby incorporated by reference.

BACKGROUND OF THE INVENTION

A counterfeit drug (or pharmaceutical, medicine) is a medication or pharmaceutical product which is produced and sold with the intent to deceptively represent its origin, authenticity or effectiveness. The World Health Organization defines a counterfeit drug as any pharmaceutical product that is deliberately mislabeled with respect to identity and/or source. Counterfeit drugs may include branded and generic products, may contain no active ingredient, the wrong active ingredient or the wrong amount of the correct active ingredient.

The U.S. Food and Drug Administration warns that "an individual who receives a counterfeit drug may be at risk of a number of dangerous health consequences. Patients may experience unexpected side effects, allergic reactions, or a worsening of their medical condition. The Centers for Disease Control and Prevention estimates that 10%-30% of medicines sold in developing countries are counterfeit.

Detecting counterfeit products is one of the ways to combat this problem. Different analytical techniques such as Fourier transform infrared spectroscopy, NIR spectroscopy, X-ray powder diffraction, thermal gravimetric analysis, microscopy, and various forms of chromatography have been used to check for frauds. Other techniques used for chemical fingerprinting to identify counterfeits include gas chromatography, ion chromatography, capillary electrophoresis, and elemental analysis. However, most of them are rather expensive and resource intensive.

BRIEF SUMMARY OF INVENTION

Embodiments of the present invention relate to systems and methods for detection of counterfeit drugs based on comparison of the isotopic composition of the tested drugs, pharmaceuticals, or medicines with the isotopic composition of the authentic products.

In one aspect of the present invention is a transformation of the tested drugs, pharmaceuticals, or medicines partially or completely into gaseous oxides by combustion reactions. A combustion reaction is the chemical term for a process known more commonly as burning. Combustion reaction is a type of chemical reaction involving two substances which usually include oxygen and heat. This approach provides a universal solution, because the absolute majority of drugs, pharmaceuticals, or medicines consist of at least one of the following elements, such as carbon, nitrogen, hydrogen, and sulfur, which produce gaseous oxides during the combustion process.

An embodiment in accordance with the present invention further comprises measurements of the isotopic compositions of the produced oxides by isotopic ratio gas analyzers based on one of the optical absorption spectroscopy methods.

The present invention provides systems and methods for determining counterfeit drugs, pharmaceuticals, or medicines.

BRIEF DESCRIPTION OF THE SEVERAL VIEWS OF THE DRAWING

FIG. 1. A method of determining counterfeit drugs, pharmaceuticals, or medicines, the method comprising of the steps of: converting the drugs, pharmaceuticals, or medicines into gaseous oxides by combustion with oxygen in a combustion chamber; delivering the produced gaseous oxides to an optical absorption spectroscopy based isotopic ratio gas analyzer and diluting them by a balance gas; measuring isotopic composition of gaseous oxides; providing data about composition of the gaseous oxides produced by combustion.

DETAILED DESCRIPTION OF THE INVENTION

One of the most precise methods of identifying counterfeit drugs pharmaceuticals, or medicines includes analysis of the chemical composition of the tested drug material and its encapsulation material. While this method can be extremely precise, it usually requires expensive equipment and complex analysis. An alternative approach is to combust (burn) a drug, a pharmaceutical, or a medicine completely in zero air or in pure oxygen, which implies converting the drug, pharmaceutical, or medicine into gas phase oxides and measuring the amount of different gaseous oxides produced during the combustion reaction and the isotopic composition of the produced gaseous oxides. Isotope composition analysis of the following oxides can be routinely performed by an optical absorption based gas analyzer: CO—Carbon Monoxide, $CO_2$—Carbon Dioxide, $N_2O$—Nitrogen Dioxide, NO—Nitric Oxide, $NO_2$—Nitrogen Dioxide, $H_2O$—Water, $H_2O_2$—Hydrogen Peroxide, $SO_2$—Sulfur Dioxide, $SO_3$—Sulfur Trioxide, and ClO—Chlorine Monoxide.

These gaseous oxides are important for analysis because carbon, nitrogen, sulfur, and hydrogen are the main atomic components of the majority of drugs, pharmaceuticals, or medicines. If liquid samples have to be tested, they can be dried out first, and then solutes can be converted to oxides by the combustion process. Solvents can also be separated from solutes and can be converted to oxides for further isotopic composition analysis of solvents. The obtained isotopic compositions can be checked with the reference isotopic compositions supplied by the drug manufacture. The obtained isotopic compositions can also be sent to a drug manufacture for confirmation of the origin of drugs, pharmaceuticals, or medicines, or sent to a third party for verification.

Embodiments of the present invention provide systems and methods for determining counterfeit drugs, pharmaceuticals, or medicines based on the transformation of the tested drugs, pharmaceuticals, or medicines into gaseous oxides. The isotopic compositions of these oxides can be precisely performed by optical absorption spectroscopy methods.

According to an embodiment, isotopic composition of gaseous oxides produced from drug, pharmaceutical, or medicine compounds can be measured by the Tuned Diode Laser Absorption Spectroscopy (TDLAS) method. Modern TDLAS based instruments provide isotopic composition measurement precisions better than 0.5‰ for $\delta 13C$ in $CO_2$ (Campbell Scientific, Inc. TGA200A Trace Gas Analyzer)

and better than 0.15‰ for δ13C in CO$_2$ (Thermo Scientific Delta Ray Isotope Ratio Infrared Spectrometer)

According to another embodiment, isotopic composition of gaseous oxides produced from drug, pharmaceutical, or medicine compounds can be measured by the Cavity Enhanced Absorption Spectroscopy (CEAS) method.

According to yet another embodiment, isotopic composition of gaseous oxides produced from drug, pharmaceutical, or medicine compounds can be measured by the Cavity Ring-Down Spectroscopy (CRDS) method. Modern CRDS based instruments provide isotopic composition measurement precisions better than 0.1‰ for δ13C in CO$_2$ (Picarro G2131-i Analyzer), 0.1‰ for δD in H$_2$O (Picarro L2140-i Analyzer), and 0.5‰ for δ15N in N$_2$O (Picarro G5131-i Analyzer).

According to an embodiment, isotopic composition of gaseous oxides produced from drug, pharmaceutical, or medicine compounds can be measured by the Integrated Cavity Output Spectroscopy (ICOS) method. Modern ICOS based instruments provide isotopic composition measurement precisions better than 0.1‰ for δ13C in CO$_2$, (LGR-ABB: Carbon Dioxide Isotope Analyzer-Elevated CO$_2$), 0.2‰ for δD in H$_2$O (LGR-ABB: Liquid Water Isotope Analyzer).

According to an embodiment, drugs, pharmaceuticals, or medicines can be transformed to gaseous oxides by combustion reactions. Combustion of the tested samples will produce oxides with isotopic composition reflecting the isotopic composition of the tested samples.

According to yet another embodiment, drugs, pharmaceuticals, or medicines in liquid form can be dried before they are conveted to gaseous oxides.

According to an embodiment, the isotopic compositions of measured oxides are compared with the isotopic compositions oxides produced from control samples.

In one aspect of the present invention, the amount of produced gaseous oxides can also be measured. These measurements provide additional and very important data about the chemical composition of the tested samples.

According to an embodiment, gaseous oxides produced during the combustion process are diluted by a balance gas. Examples of balance gases are: nitrogen, oxygen, helium, neon, argon, zero air. The dilution step may be required if concentrations of the produced oxides are too high for the optimal operation of an optical absorption spectroscopy based isotopic ratio analyzer. It is important that the dilution step doesn't change isotopic compositions of gaseous oxides.

FIG. 1 shows a schematic of a system for drugs, pharmaceuticals, or medicines authenticity verification, the system comprising: a combustion chamber for converting the tested drugs, pharmaceuticals, or medicines into gaseous oxides, a source of oxygen, and an optical absorption spectroscopy based isotopic ratio gas analyzer to measure said gaseous oxides produced in the combustion chamber, wherein the system is capable to dilute gaseous oxides formed through the combustion process by a balance gas Taking into account that the combustion process can be easily standardized and the modern isotopic ratio analyzers are quite precise and accurate, the proposed method may become a very powerful tool to distinguish counterfeit drugs, pharmaceuticals, and medicines from authentic products.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the disclosed subject matter (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or example language (e.g., "such as") provided herein, is intended merely to better illuminate the disclosed subject matter and does not pose a limitation on the scope of the invention unless otherwise claimed. No language in the specification should be construed as indicating any non-claimed element as essential to the practice of the invention.

Certain embodiments are described herein. Variations of those embodiments may become apparent to those of ordinary skill in the art upon reading the foregoing description. The inventors expect skilled artisans to employ such variations as appropriate, and the inventors intend for the embodiments to be practiced otherwise than as specifically described herein.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A method of verifying authenticity of a drug, a pharmaceuticals, or a medicine, the method comprising the steps of: a) forming a gaseous oxide through combustion of the drugs, pharmaceuticals, or medicines with a gas containing molecular oxygen; b) delivering a sample of a gas mixture containing the gaseous oxide to an isotopic ratio gas analyzer; c) measuring a value proportional to the ratio of a number of molecules of a first isotopologue of the oxide in the sample to a number of molecules of a second isotopologue of the gaseous oxide in the sample; d) making a conclusion based on the measured value and an isotopic composition of an authentic product, wherein said gaseous oxides selected from the group consisting of: CO, CO$_2$, N$_2$O, NO, NO$_2$, H$_2$O, H$_2$O$_2$, SO$_2$, SO$_3$, ClO.

2. The method of claim 1, wherein the gas containing molecular oxygen is a gas containing molecular oxygen with a known isotopic composition of oxygen.

3. The method of claim 1, further including measuring an amount of the gaseous oxides formed through the combustion.

4. The method of claim 1, further including dilution of the gaseous oxide formed through the combustion by a balance gas.

5. The method of claim 1, wherein forming the gaseous oxide through combustion includes removing a solvent from the drug, pharmaceutical, or medicine in a form of a liquid solution, and converting a solid residual into a gaseous oxides by combustion.

6. The method of claim 1, wherein forming the gaseous oxide through combustion includes removing a solvent from the drug, pharmaceutical, or medicine in a form of a liquid solution, and converting the solvent into a gaseous oxide by combustion.

7. The method of claim 1, wherein the isotope ratio gas analyzer is based on the Tuned Diode Laser Absorption Spectroscopy method.

8. The method of claim 1, wherein the isotope ratio gas analyzer is based on the Cavity Enhanced Absorption Spectroscopy method.

9. The method of claim 1, wherein the isotope ratio gas analyzer is based on the Cavity Ring-Down Spectroscopy method.

10. The method of claim 1, wherein the isotope ratio gas analyzer is based on the Integrated Cavity Output Spectroscopy method.

11. The method of claim 1, wherein the isotope ratio gas analyzer is based on the Photo-Acoustic Spectroscopy method.

\* \* \* \* \*